(12) United States Patent
Burton

(10) Patent No.: US 7,827,873 B2
(45) Date of Patent: Nov. 9, 2010

(54) SOIL SAMPLING APPARATUS AND METHOD

(76) Inventor: James D. Burton, 649 Jackson 917, Newport, AR (US) 72112

( * ) Notice: Subject to any disclaimer, the term of this patent is extended or adjusted under 35 U.S.C. 154(b) by 79 days.

(21) Appl. No.: 12/371,400

(22) Filed: Feb. 13, 2009

(65) Prior Publication Data

US 2010/0037712 A1    Feb. 18, 2010

Related U.S. Application Data

(63) Continuation-in-part of application No. 11/825,483, filed on Jul. 6, 2007, now Pat. No. 7,552,654, which is a continuation of application No. 10/548,907, filed as application No. PCT/US2004/007183 on Mar. 9, 2004, now Pat. No. 7,255,016.

(60) Provisional application No. 60/454,460, filed on Mar. 13, 2003.

(51) Int. Cl.
*G01N 1/04* (2006.01)

(52) U.S. Cl. .............. 73/864.45; 73/864.32; 73/864.41; 73/864.44; 173/19; 173/24; 173/25; 175/20

(58) Field of Classification Search .................. 73/863, 73/864, 864.31, 864.32, 864.41–864.45
See application file for complete search history.

(56) References Cited

U.S. PATENT DOCUMENTS

| | | |
|---|---|---|
| 1,362,968 A | 12/1920 | Stewart |
| 2,565,224 A | 8/1951 | Gibbens |
| 3,084,553 A | 4/1963 | Cullinan et al. |
| 3,224,512 A | 12/1965 | Alexander |
| 3,331,249 A | 7/1967 | Boxrud |
| 3,464,504 A | 9/1969 | Stange |
| 3,625,296 A | 12/1971 | Mabry |
| 4,316,393 A | 2/1982 | Philipenko |
| RE30,901 E | 4/1982 | Boxrud |
| 4,332,301 A | 6/1982 | Jonell |
| 4,333,541 A | 6/1982 | Doty |
| 4,336,849 A | 6/1982 | Hug |
| 4,356,734 A | 11/1982 | Ivancsics |
| 4,482,021 A | 11/1984 | Repski |
| 4,828,047 A | 5/1989 | Rogerson |
| 4,869,115 A | 9/1989 | Edwards et al. |
| 4,989,678 A | 2/1991 | Thompson |
| 5,076,372 A | 12/1991 | Hellbusch |
| 5,211,248 A | 5/1993 | Nosewicz et al. |
| 5,213,169 A | 5/1993 | Heller |

(Continued)

FOREIGN PATENT DOCUMENTS

SU        643771 A  *  1/1979

(Continued)

*Primary Examiner*—David A. Rogers
(74) *Attorney, Agent, or Firm*—J. Charles Dougherty

(57) ABSTRACT

An apparatus automatically removes soil samples at intervals over a field of interest. The apparatus comprises a sampling assembly that rotates on a track. The probe of the sampler assembly is extended through the track and into the ground, then retracted on each revolution of the track. The sampler assembly is hinged and guided along a track in order to minimize soil compaction as the probe rotates around the rear wheel of the apparatus. Soil is ejected by means of a "rumble path" along the top of the track. The soil samples are pneumatically transferred to a bagging assembly located in the tractor pulling the apparatus.

27 Claims, 10 Drawing Sheets

U.S. PATENT DOCUMENTS

| | | | |
|---|---|---|---|
| 5,394,949 | A | 3/1995 | Wright et al. |
| 5,435,399 | A | 7/1995 | Peterson et al. |
| 5,741,983 | A | 4/1998 | Skotnikov et al. |
| 5,887,491 | A | 3/1999 | Monson et al. |
| 5,950,741 | A | 9/1999 | Wright et al. |
| 6,016,713 | A | 1/2000 | Hale |
| 6,119,531 | A | 9/2000 | Wendte et al. |
| 6,237,429 | B1 | 5/2001 | Melnyk |
| 6,260,633 | B1 | 7/2001 | Machek et al. |
| 6,360,829 | B1 | 3/2002 | Naber et al. |
| 6,363,803 | B1 | 4/2002 | Hubers |
| 6,688,245 | B2 | 2/2004 | Juptner |
| 6,766,865 | B1 | 7/2004 | Dagel et al. |
| 6,959,245 | B2 | 10/2005 | Rooney et al. |
| 7,047,133 | B1 | 5/2006 | Dyer et al. |
| 7,047,135 | B2 | 5/2006 | Dyer et al. |
| 7,184,892 | B1 | 2/2007 | Dyer et al. |
| 2005/0172733 | A1 | 8/2005 | Drummond et al. |

FOREIGN PATENT DOCUMENTS

SU 823949 B * 4/1981

* cited by examiner

SOIL SAMPLING APPARATUS AND METHOD

CROSS-REFERENCE TO RELATED APPLICATIONS

This application is a continuation-in-part and claims the benefit of U.S. utility patent application Ser. No. 11/825,483, filed on Jul. 6, 2007 and entitled "Soil Sampler Apparatus and Method," which in turn is a continuation of and claims the benefit of U.S. utility patent application Ser. No. 10/548,907, filed on May 8, 2006 and entitled "Soil Sampler Apparatus and Method," now U.S. Pat. No. 7,255,016 issued on Aug. 14, 2007, which in turn claimed the benefit of international patent application no. PCT/US2004/007183, entitled "Soil Sampler Apparatus and Method" and filed on Mar. 9, 2004, which in turn claimed the benefit of U.S. provisional patent application No. 60/454,460, filed Mar. 13, 2003 and entitled "Soil Sampler." The disclosure of each of such foregoing applications are incorporated herein by reference.

STATEMENT REGARDING FEDERALLY SPONSORED RESEARCH OR DEVELOPMENT

Not applicable.

BACKGROUND OF THE INVENTION

The present invention relates to soil sampling devices and methods, and in particular to soil sampling devices that periodically and automatically take soil samples over an area of interest and store them for later analysis, and related methods.

In order to optimize the production capacity of any agricultural land, the grower must provide in each plot of soil the amount of fertilizers and other nutrients and additives that will render each plot ideal for the crop that is to be sewn and harvested. The grower cannot know how much fertilizer or other additives should be placed at a plot of soil, however, without knowing the current level of nutrients and important minerals that are already present in each plot. The quantity of these various materials present will vary greatly depending upon such factors as the soil type, the history of crops grown, and additives that have been previously applied to the field. It is thus a common practice for growers to periodically remove soil samples from various regions on their agricultural lands, which are then analyzed to determine the level of various important nutrients and minerals that they contain. It would also be highly desirable to know the level of compaction of soil in various regions, in order to properly gauge the steps necessary to arrive at the proper level of soil compaction for a particular crop to be grown in each region, although this testing is not commonly performed today.

Soil sampling has historically been a process performed by hand. Various hand tools have been developed to somewhat ease the burden of this task, but any manual operation to perform soil sampling is necessary tiresome and time-consuming because of the expanse of land that must be covered when soil sampling is performed as part of a large-scale commercial farming enterprise. Not only must a worker remove each sample, but the sample must then be transported back to a laboratory for analysis, and the samples must be transported in such a manner that samples from various plots are not mixed. Further, the samples must each be carefully labeled, and the worker must keep close track of his or her location when each sample is removed. Because of the arduous nature of this task, growers typically take only one sample in a field of interest, or at most a few samples across a field or area of interest and then average the results. The farmer will then apply fertilizers and other nutrients to the soil as if the soil's level of nutrients were uniform across the field, which is in fact not generally the case. The result is a poor approximation of the optimal nutrient level for each plot of soil, since some plots will likely be under fertilized and others will be over fertilized. Under fertilized plots will produce poor yields, and over fertilized plots may both produce poorer than optimum yields and also result in a waste of fertilizers. The wasted fertilizer not only is an added expense for the grower, but also exacerbates environmental issues that may arise from the later run-off of the excessive fertilizer due to rain or wind.

With the wide availability of global positioning system (GPS) satellite receivers today, the use of GPS information in soil sampling is rapidly increasing. GPS receivers have in fact become a staple of modern commercial farming equipment. The use of GPS in conjunction with manual soil sampling, however, only provides modest improvements in accuracy and efficiency. Although the grower now has precise information about where each sample is taken, manual sampling procedures still require a worker to travel to each identified point in the field of interest, remove a sample by hand, and then label and transport that sample for analysis. Thus it would be highly desirable to develop a soil sampling system that would periodically sample the soil across a field, while automatically keeping track of where samples were removed using GPS information, and automatically separating the samples according to location for ease of analysis. Such a system would ideally allow the operator to simply program the sampling mechanism for movement around the field or fields of interest in a regular pattern, while the mechanism performs sampling in a manner that is automatic and effectively transparent to the operator.

The related art includes several attempts to develop soil sampling mechanisms that periodically sample soil over an area. U.S. Pat. No. 3,224,512 to Alexander teaches a soil sampler that is mounted on a trailer and powered by a hydraulic system. The device is intended to be pulled by a tractor around a field, and the motion of one of the vehicle wheels activates a piston and cam-drive arrangement in communication with the soil sampler's hydraulics. Since the sampling periodicity is driven by the motion of one of the wheels on the trailer, the device automatically samples soil at regular intervals, regardless of the speed of the tractor pulling the trailer. The device uses a sampling tube that is forced into the ground for sample collection. Since the device does not stop in order for samples to be taken, the sampling tube is designed to pivot upon entry into the ground. The sampling tube is returned to its original insertion position (angled toward the front of the trailer) by means of a spring.

U.S. Pat. No. 3,625,296 to Mabry et al. teaches another soil sampling device that is mounted on a trailer, and which is intended to periodically sample soil over which the trailer passes. A digger foot is used to collect the soil sample, the foot being mounted at the end of a lever that includes a cam follower at its opposite end. By means of the cam follower, a cam on one of the tractor's wheels forces the digger foot into the ground as the trailer travels, thereby scooping a soil sample. As the cam rolls forward, the digger foot is released and a spring biases the digger foot upward, where it strikes a bumper block and deposits the soil sample into a collection container. Like the Alexander device, the Mabry et al. device automatically samples soil at regular intervals, since its sampling periodicity is driven by the distance traveled by the cam-equipped tractor wheel.

U.S. Pat. No. 5,741,983 to Skotnikov et al. teaches a third trailer-mounted automatic soil sampling device. In this case, an odometer is used to monitor the distance of travel of the trailer, which drives the sampling period of the device. The device utilizes a shaft-drive and linkage arrangement to control the period of the sampling action based upon the rotation of one of the trailer's wheels. A complex linkage arrangement allows the sampling tube to be raised into a position to eject and deposit a sample during each sampling cycle. The device further includes a bagging mechanism, whereby each of the samples that are drawn from the ground may be automatically bagged and labeled for later laboratory analysis.

The automatic sampling mechanisms described above suffer from important disadvantages that have limited their adoption in large commercial farming operations. Mechanisms that simply scoop a sample of material from the top of the ground are undesirable, since such a sample may not be representative of the lower levels of the soil in the area that is sampled. The most relevant section of the soil is that section that will be in greatest contact with the roots of the crop to be planted, which in the case of almost all commercial crops will be soil that lies at some distance below the surface. Further, in many applications the most desirable sample will be one that spans a section of the soil, from the surface to a pre-determined depth beneath the surface. A scooping mechanism will likely be unable to probe deeply enough to produce a sufficient sample to meet this need.

Although sampling mechanisms that insert a tube into the ground to collect a sample are superior to scoop mechanisms in many applications, the tube-type sampling mechanisms known in the art also suffer from important disadvantages. It is desirable in an automatic sampling mechanism that the sample be taken without requiring the vehicle that is carrying the sampling mechanism to stop. This greatly simplifies the task of the operator of the vehicle, since sampling can be automatically performed as the vehicle follows a pre-determined course over a field of interest, and also because it will save the operator a significant amount of time during the sampling process. The process of inserting and removing a tube from a moving vehicle, however, presents a number of difficulties. In one case these difficulties have been addressed by the use of a tube that pivots, thereby allowing the tube to be inserted into the ground at a forward-sloped angle, while it pivots rearwardly until the tube is removed. Depending upon the hardness of the soil, however, this may create a great deal of stress upon the tube. The pivoting action causes the tube to push backward against soil that is rearward of the tube at its distal end, and push forward against soil that is forward of the tube at its proximal end. While this may be a workable solution in very loose, highly compressible soil, this will likely lead to bending, excessive wear, or other damage to the tube in more firmly packed soil, such as many clay-based soils, or soil that may contain rocks or other hard obstacles.

Another solution to the problem of vehicle motion while the tube is inserted in the ground is a complex linkage arrangement that allows the structure immediately supporting the sampling tube to "follow" the tube during the portion of the sampling cycle when the tube is inserted into the ground. While this arrangement may avoid the problems presented by tube rotation, the structure and linkages necessary for this functionality are complex, and would likely be expensive to manufacture and difficult to maintain.

Regardless of how the tube is inserted in the ground, the prior art does not disclose a simple, efficient means to remove soil from the sampling tube once it is removed from the ground. Depending upon the composition and moisture content of the soil, the soil may be prone to stick within the tube. In addition, movement of the tube after the sample is withdrawn from the soil may cause compaction in the tube. The addition of a mechanical ejectors adds significant complexity to the sampling machine, and it would be desirable therefore to avoid the necessity of a mechanical ejector while maintaining consistent, smooth ejection across a variety of soil types and moisture levels.

Another disadvantage of the systems described above is that they do not take advantage of the efficiencies that may be achieved with the use of GPS information during sampling. Mapping of a field of interest, and selection of areas within the field for individual analysis, is greatly simplified using GPS information, and furthers the goal of making the process as transparent and automatic for the operator as possible.

What is desired then is an automatic soil sampling mechanism that facilitates the sampling of soil across an area of interest by simply tracing the mechanism over the area, while also being inexpensive to manufacture and simple to maintain, and taking advantage of GPS information. The limitations of the prior art are overcome by the present invention as described below.

SUMMARY OF THE INVENTION

The present invention is directed to an automatic soil sampling apparatus that comprises a sampling assembly that revolves around a continuous track while the apparatus is in motion. The apparatus may preferably be pulled behind a tractor to provide locomotion, the tractor forming a part of the apparatus in use. The sampling assembly revolves with the continuous track of the drive mechanism, allowing it to retrieve soil samples as it passes over the ground during each revolution. The sampling assembly will in effect be stationary with respect to the ground as it is passing along that portion of the continuous track's path that is in contact with the ground, and thus the sampling tube of the sampling assembly may be inserted into the ground and removed while passing along the bottom portion of the drive, without the need for a pivoting action or complex linkages in order to hold the tube in a particular position while the sample is collected. A rail or guide arrangement, against which the sampling assembly rides, may be used in various embodiments to extend and retract the sampling tube. The sample may be dropped from the sampling tube as it passes around the top portion of the drive mechanism. In various embodiments, soil compaction within the sampling tube may be avoided by careful design of the track along which the sampling assembly rides and tapering of the interior of the tube itself. Soil may, in certain embodiments, be removed from the sampling tube without the need for complex mechanical ejectors by the use of a "rumble path" that shakes the sampling assembly as it passes along the top portion of its path around the track of the device.

Soil cores dropped from the sampling tube fall into a collection trough, which in certain embodiments may include an auger system to direct soil. A pneumatic delivery system may be used in certain embodiments to move collected samples from the collection tray to sample storage bags, which for ease of access may be located adjacent to the operator of a vehicle pulling the sampling mechanism. In one embodiment, a rotating carousel with multiple bag holders may be employed in order to collect samples. In another embodiment, a continuous bag maker is employed to separate each soil sample into its own bag in a "sausage-link" arrangement. A computer-based GPS mapping system may be used in conjunction with the present invention in order to coordinate the mapping of a field of interest and collection of samples at appropriate locations, as well as guiding the pull vehicle.

It is therefore an object of the present invention to provide for a soil sampling mechanism that may automatically collect soil samples over an area of interest.

It is a further object of the present invention to provide for a soil sampling mechanism that provides sampling tubes that are stationary with respect to the ground during a portion of the sampling cycle so that the tube may be easily inserted and retracted from the ground in order to collect samples.

It is also an object of the present invention to provide for a soil sampling mechanism that is inexpensive to produce and easy to maintain.

It is also an object of the present invention to provide for a soil sampling mechanism that allows for the pneumatic movement of collected samples from a collection tray to a location more convenient to an operator.

It is also an object of the present invention to provide for a soil sampling mechanism that allows the automatic collection of a number of soil samples in a plurality of separate bags for later analysis.

It is also an object of the present invention to provide for a soil sampling mechanism that allows for the use of a computer-based mapping system in order to map an area of interest and collect samples from the appropriate portions of the area of interest.

These and other features, objects and advantages of the present invention will become better understood from a consideration of the following detailed description of the preferred embodiments and appended claims in conjunction with the drawings as described following:

DETAILED DESCRIPTION OF THE PREFERRED EMBODIMENTS

Figure 1:
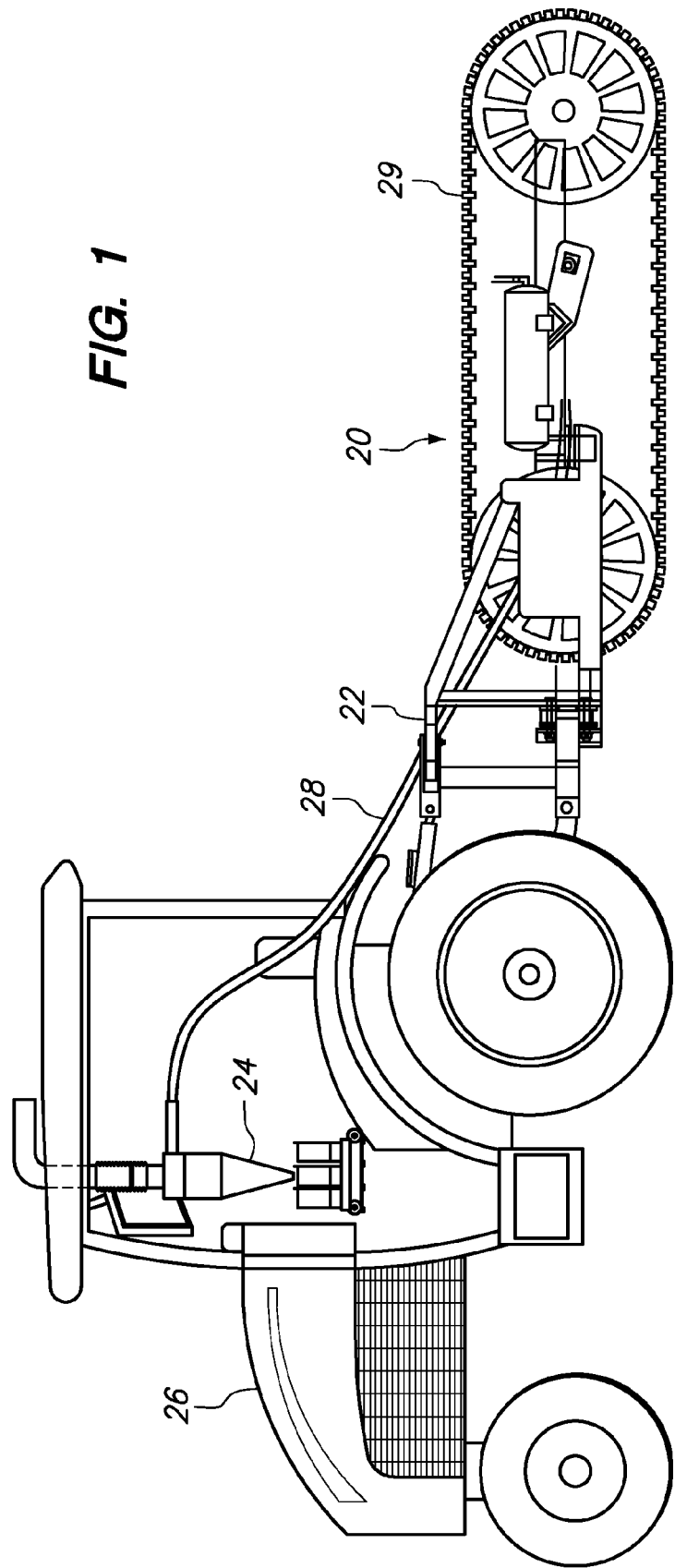
FIG. 1 is a side elevational view of the overall soil collection apparatus with tractor for locomotion, according to a preferred embodiment of the present invention.

With reference to FIG. 1, an overview of the preferred embodiment of the present invention may be described. Sampler assembly 20 is attached to tractor 26 by means of hitch assembly 22. As will be described in greater detail following, sampler assembly 20 is the mechanism that collects soil samples as track 29 turns while in contact with the ground. While in the preferred embodiment the rotational drive member of the invention is provided by a rubber track 29, many other drive means may be employed in alternative embodiments. Metal tracks could be employed, which are commercially available. Another embodiment may feature a pair of roller chains that rotate about sprocket pairs, with cross pieces fitted between the roller chains forming in effect a track-type arrangement. Channel iron in a "C" shape may be ideal for this embodiment since the rides forming the arms of the "C" shape may be faced outwardly in order to provide traction. In another alternative embodiment, track 29 may be replaced simply with wheels that contact the ground and transfer their rotational energy, through mechanical linkages or otherwise, to a set of sprockets or wheels that drive the revolution of the sampling mechanism. In yet another alternative embodiment, a powered drive system may be employed, such that the sampling mechanism rotates under power from a motor, engine, or the like, and no direct contact between the ground and any drive mechanism is in fact required. Tractor 26 can be of any type that is capable of pulling sampler assembly 20 across a tract of agricultural land, including trucks and small utility vehicles, but in the preferred embodiment is a smaller tractor of the sort used for conventional farming applications. Such tractors commonly employ standardized three-point hitches, and in the preferred embodiment this type of hitch is used to connect tractor 26 to hitch assembly 22. The three-point hitch of tractor 26 may be used to raise or lower sampler assembly 20; when raised, sampler assembly 20 will not be in contact with the ground, and soil samples will not be taken, while lowering sampler assembly 20 causes rotation of track 29 due to contact with the ground, thereby causing samples to be collected. Bagger assembly 24 is preferably mounted in the cab section of tractor 26, within reach of the operator seated in tractor 24. Bagger assembly 24 receives soil from sampler assembly 20, while sampler assembly 20 is in the lowered position, by means of pneumatic line 28, in a manner that will be described more fully below. In alternative embodiments, bagger assembly 24 may be mounted outside of the cab or on sampler assembly 20.

Figure 2:
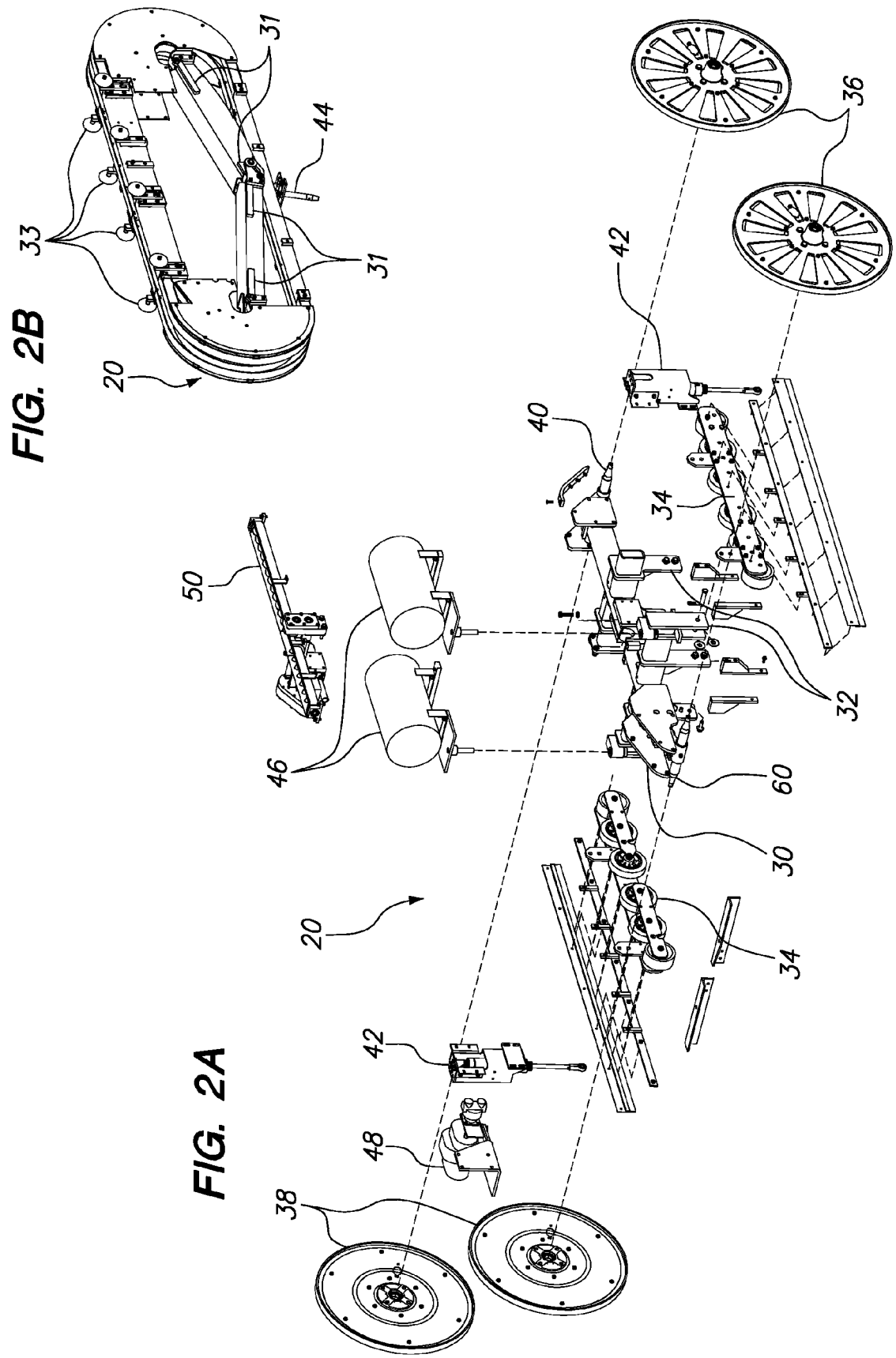
FIG. 2A is a perspective, exploded view of several major components of a sampler assembly according to a preferred embodiment of the present invention.
FIG. 2B is a perspective view in partial cut-away of certain components of a sampler assembly according to a preferred embodiment of the present invention.

Referring now to FIGS. 2A and 2B, certain components of sampler assembly 20 of a preferred embodiment of the present invention may be described. Main frame 30 provides a mounting point for various other components of sampler assembly 20. Bogey wheel supports 32 connect main frame 30 to the left-hand and right-hand bogey wheel assemblies 34. The function of bogey wheel assemblies 34 is to provide support for track 29 as it passes along the ground during operation of sampler assembly 20. In the preferred embodiment illustrated in FIG. 1, six bogey wheels are fitted at each of bogey wheel assemblies 34, but a different number of wheels may be employed in alternative embodiments. Various other types of track support wheels are known in the art, and may be substituted in alternative embodiments. Main wheels halves left 36 and main wheel halves right 38 are fitted at axles 40 on main frame 30, and provide support for track 29 at either end of sampler assembly 20. Upper guide wheels 33, shown in FIG. 2B, provide support for track 29 at the top of sampler assembly 20. It may be understood then that track 29 passes in a rotating fashion around the bogey wheels, main wheels, and upper guide wheels 33 of sampler assembly 20.

Lift cylinders 42 are fitted at either side of main frame 30, as shown in FIG. 2A, and provide lift to prevent damage to probe assembly 44 if a hard object is struck as probe assembly 44 attempts to collect a soil sample. Lift cylinders 42 are pneumatically powered by compressed air stored in storage cylinders 46, which are also mounted at main frame 30. A 12-volt or power take-off (PTO) air compressor (not shown) may be employed to provide compressed air to storage cylinders 46, such devices being well known in the art. Load cells 31, which are shown in FIG. 2B, may be of any conventional sort as understood in the art, the function of which is to output an electrical signal corresponding to the force being exerted on the cell. In the case of the preferred embodiment of the present invention, the purpose of load cells 31 is to measure the upward force being exerted on probe assembly 44 as the probe enters the soil to collect a sample. A control system (not shown) sums the totals from four load cells 31 and checks to determine if the load has exceeded a threshold value. In a preferred embodiment, this threshold may be about 800 pounds. If the threshold is exceeded, lift cylinders 42 are activated, lifting probe assembly 44 so that the probe is not forced into the ground. If the excessive force is caused, for example, by an obstruction, then lifting of probe assembly 44 prevents damage to the probe that might be caused by forcing probe assembly 44 downward despite the presence of the obstacle. The readings from summing the outputs of load cells 31 may also be optionally employed in conjunction with a controller to measure the level of soil compaction as each soil core is removed. These results may be combined with a computer to form, for example, a color-coded map visually demonstrating the soil compaction levels in the various parcels of the agricultural tracts over which the device collects samples.

Additional elements of sampler assembly 20 as shown in FIG. 2A include blower 48 and collection assembly 50. As more fully explained below, collection assembly 50 serves to catch soil that is ejected from probe assembly 44 as it passes along the top portion of sampler assembly 20 during the collection process. Blower 48 provides low-pressure air to rotor assembly 86, which drives collected soil samples from collection assembly 50 toward bagger assembly 24.

Figure 3:
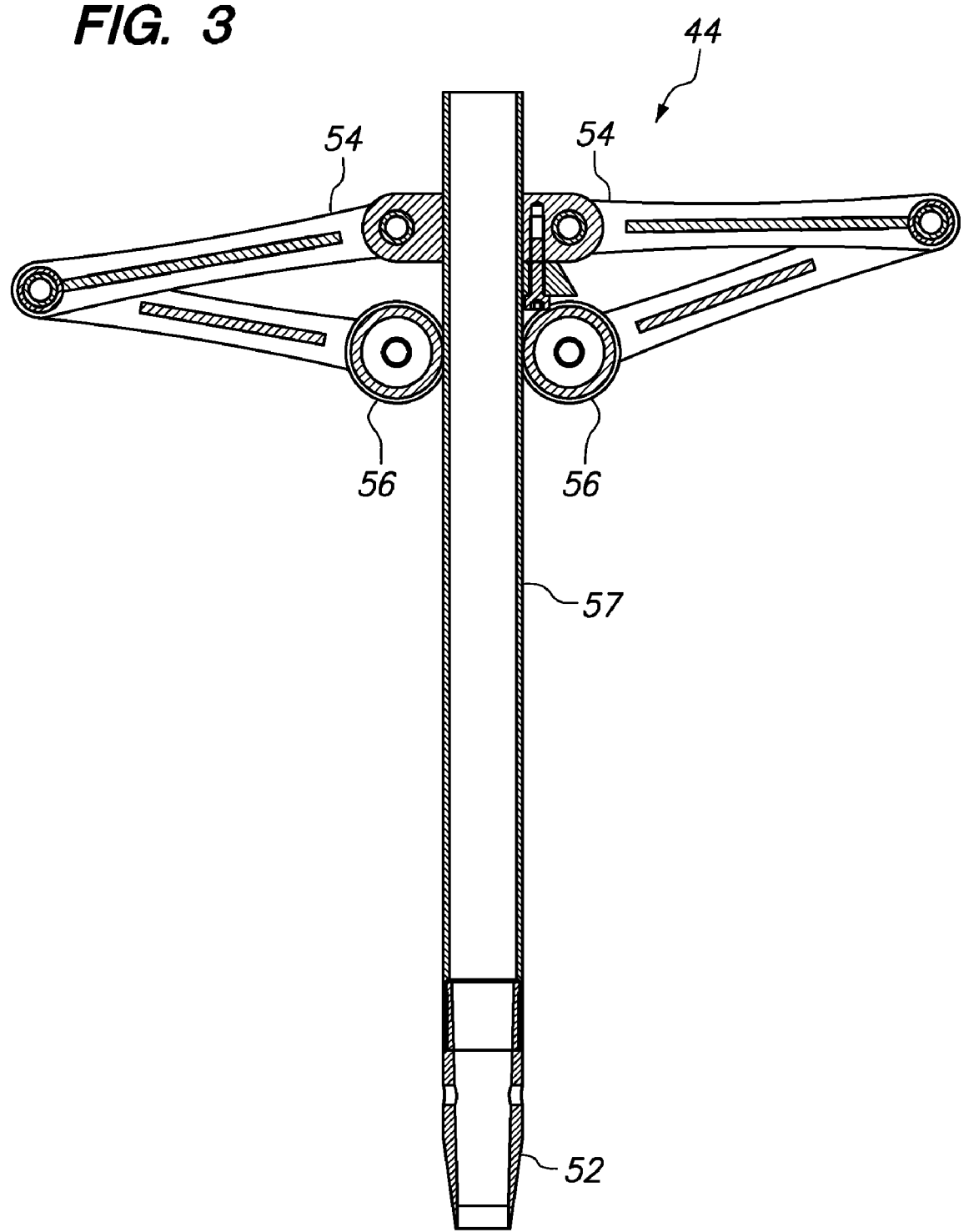
FIG. 3 is a side elevational view, in partial cut-away, of a sampler assembly according to a preferred embodiment of the present invention.
Figure 4:
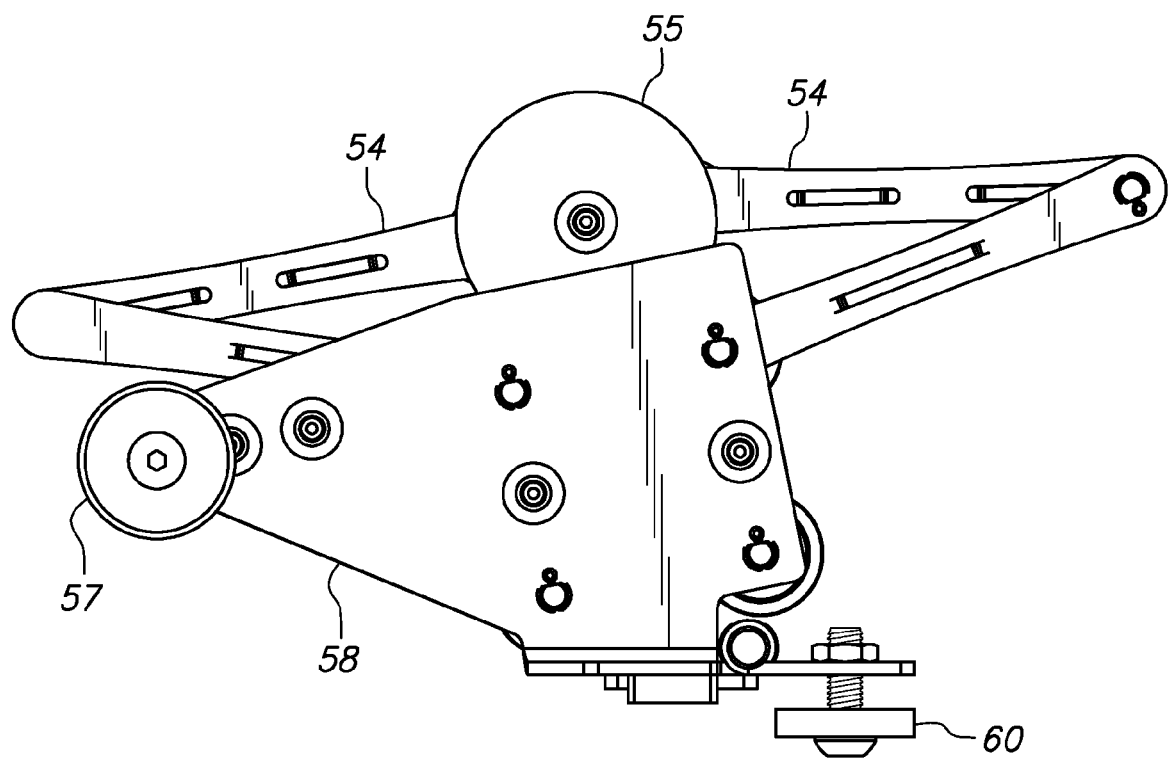
FIG. 4 is a side elevational view of the sampler assembly and track mounting arrangement according to a preferred embodiment of the present invention.

Turning now to FIGS. 3 and 4, major components of probe assembly 44 according to a preferred embodiment of the present invention may be described. Probe 51 is a hollow tube, designed to receive soil upon its insertion into the ground during sampling operation. Probe 51 may be constructed of any sufficiently rigid and durable material, such as steel. Probe tip 52 is attached at the distal end of probe 50. In alternative embodiments, probe 51 and probe tip 52 may be constructed as a single part, although it is preferred that they are separate so that probe tip 52 may be easily replaced as it wears during sampling operations. It will be noted that the interior of probe tip 52 in the preferred embodiment is sloped such that the inner diameter increases as soil pushes into tip 52, the purpose of which is to prevent soil compaction, as will be explained in greater detail below. Scissor arms 54 are hinged to probe 52, thereby allowing probe 52 to extend and retract during sampling operation as will be described following. Probe arm wheels 56 on each of scissor arms 54 guide probe 50 as it extends and retracts. Probe brackets 58, attached at each side of probe assembly 44 as shown in FIG. 4, provide a connection point between probe assembly 44 and track 29. Probe rollers 55 are positioned at each side of probe 52, between probe 52 and probe brackets 58. Follower rollers 57 extend from the outside edges of each of probe brackets 58. Probe hinge assembly 60 connects probe brackets 58 to track 29. Probe hinge assembly 60 allows the angle of probe 52 to change as probe assembly 44 rotates around sampler assembly 20, carried by track 29.

Figure 5:
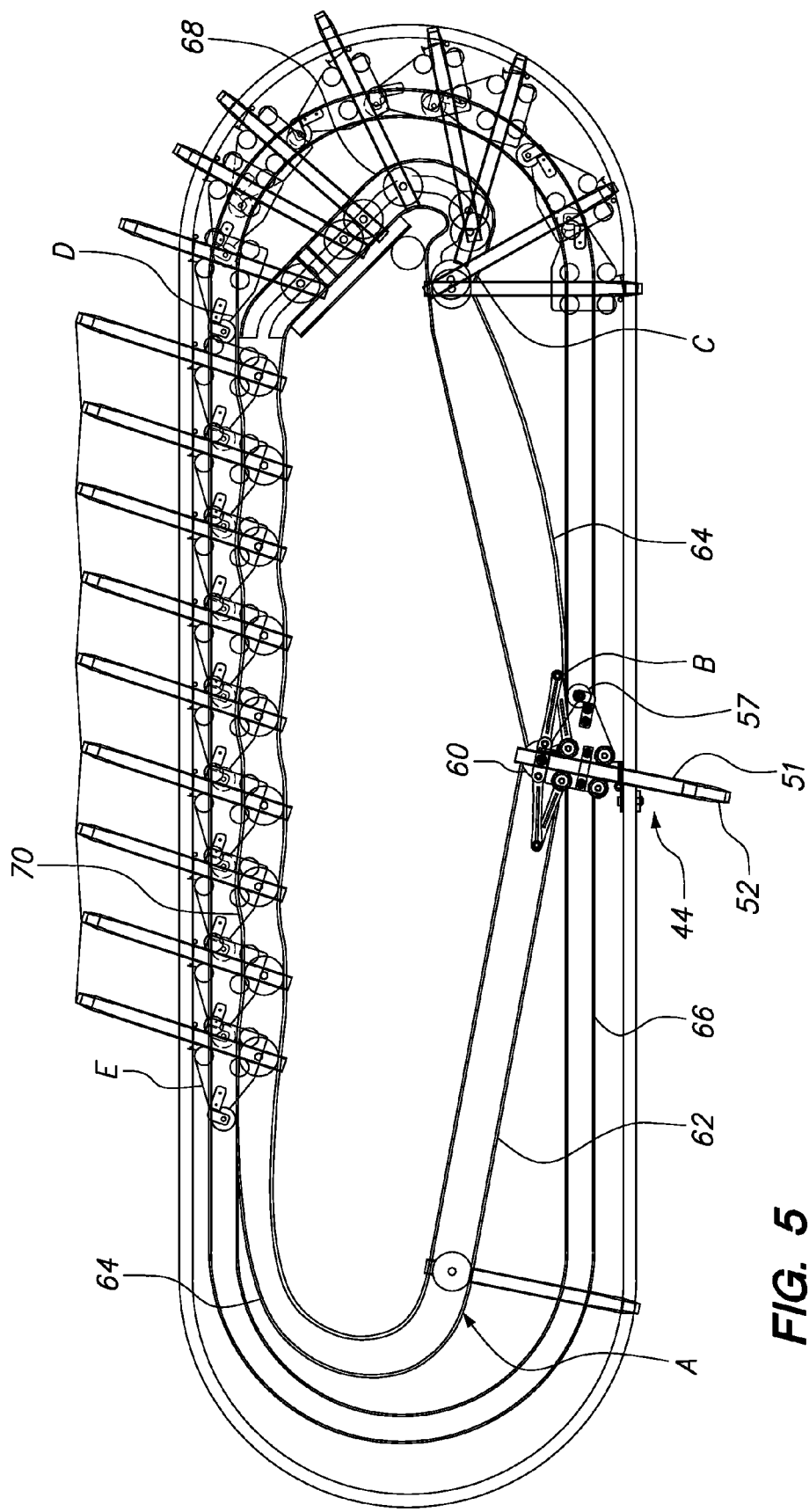
FIG. 5 is a diagram illustrating the motion of the sampler assembly around the track course of the sampler assembly according to a preferred embodiment of the present invention.

FIG. 5 illustrates the path of probe assembly 44 as it turns in conjunction with the movement of track 29 during a sampling operation. At position A, probe assembly 44 is in the fully retracted position, such that probe tip 52 does not extend beyond the exterior side of track 29. As probe assembly 44 moves from position A to position B, it follows forward probe track 62 by means of probe rollers 55, and probe follower track 66 by means of follower rollers 57. Since probe track 62 is progressively closer to the position of probe follower track 66, and hence track 29, as probe assembly 44 moves from position A to position B, this motion causes scissor arms 54 to gradually retract, thereby pushing probe tip 52 outward through an opening in track 29 and into the soil. At position B, scissor arms 54 are fully retracted, and probe 52 is fully extended into the ground, the depth of probe tip 52 in the ground being about six to twelve inches in the preferred embodiment. The actual preferred depth will depend upon the soil conditions and the crop to be grown on the associated tract of land. It will be seen that as probe assembly 44 reaches position B, soil is collected within probe 51 and probe tip 52.

Beginning at position B and moving toward position C, it may be seen that the paths of probe rollers 55 in rearward probe track 64, and follower rollers 57 in probe follower track 66, causes probe tip 52 to begin to withdraw from the ground. Soil is captured within probe 51 and probe tip 52, and is thereby withdrawn from the ground as a sample during this movement. It should be noted that rearward probe track 64 is sloped, rather than straight as is forward probe track 62. The purpose of this curvature is to prevent a sudden reverse acceleration of probe 51, which could lead to compaction of the soil within probe 51. The curvature of rearward probe track 64 is preferably chosen such that the velocity with which probe 51 retracts from the soil rises at a constant rate, that is, the upward acceleration of probe 51 is constant between points B and C. This construction is believed to minimize the compaction of soil within probe 51 and tip 52 that results from the withdrawal of probe 51 from the soil. When point C is reached, scissor arms 54 will again be fully extended and probe tip 52 will be fully withdrawn from the ground. It should be noted that because probe assembly 44 moves with track 29, there is little or no shear force acting on probe 51 as it is inserted and withdrawn from the soil, since probe assembly 44 is effectively moving at zero forward velocity with respect to the soil during this part of the sampling operation.

As probe assembly 44 moves from position C to position D, it is brought with the adjacent portion of track 29 around rearward main wheel halves 36 and 38. The path of probe follower track 66 during this section follows a smooth curve, but the path of upward probe track 68 is generally hook-shaped, as illustrated in FIG. 5. The purpose for this shape is to minimize the centrifugal force that acts upon soil resting within probe 51 and probe tip 52. It is believed that allowing probe 51 to simply swing in a smooth curve as it passes around the rear of sampler assembly 20 serves to compact the soil within probe tip 52, due to the significant centrifugal forces acting upon the soil during this movement, particularly that portion of the soil at the distal end of probe 51 and within probe tip 52. The shape illustrated in FIG. 5, however, causes probe 51 to be pointed more upwardly than it would if a smooth curve were employed as it passes around rear axle 40. This position prevents or reduces compaction of soil within probe tip 52 due to centrifugal force, allowing the soil to more easily be removed from the proximal end of probe 51 in subsequent steps of the sampling operation. It may be noted that probe hinge assembly 60 allows probe assembly 44 to pivot with respect to track 29, thus allowing probe assembly 44 to smoothly follow the path of upward probe track 68. As probe assembly 44 reaches position D, it is pointed in a generally upward direction, and preferably is partially extended through track 29 since upward probe track 68 begins to approach probe follower track 66 as position D is approached.

Moving probe assembly 44 now from positions D to E as shown in FIG. 5, the soil sample collected earlier may be removed from probe 51. Top probe track 70 contains a series of ridges, bumps, or the like, producing a "rumble path" through which probe assembly 44 passes as it moves across the top of sampler assembly 20. The purpose of the rumble path is to shake the collected sample within probe 51 such that it is ejected below probe 51, falling into collection assembly 50. This mechanism thus obviates the need for a separate mechanical ejector in conjunction with probe 51. Preferably, the ridges, bumps, or the like within top probe track 70 are structured such that a gradual rise is followed by an abrupt fall, as illustrated in FIG. 5. The abrupt fall causes probe assembly 44 to jerk downward with significant force and then stop abruptly, which serves to eject the soil sample within probe 51 downward more forcefully. By the time probe assembly 44 reaches position E, substantially all of the soil previously collected within probe 51 has been ejected into collection assembly 50, and probe 44 is ready to collect another sample. Probe assembly 44 returns to position A as it turns around forward axle 40 by means of downward probe track 64 guiding probe roller 55 and probe follower track 66 again guiding follower roller 57.

Figure 6:
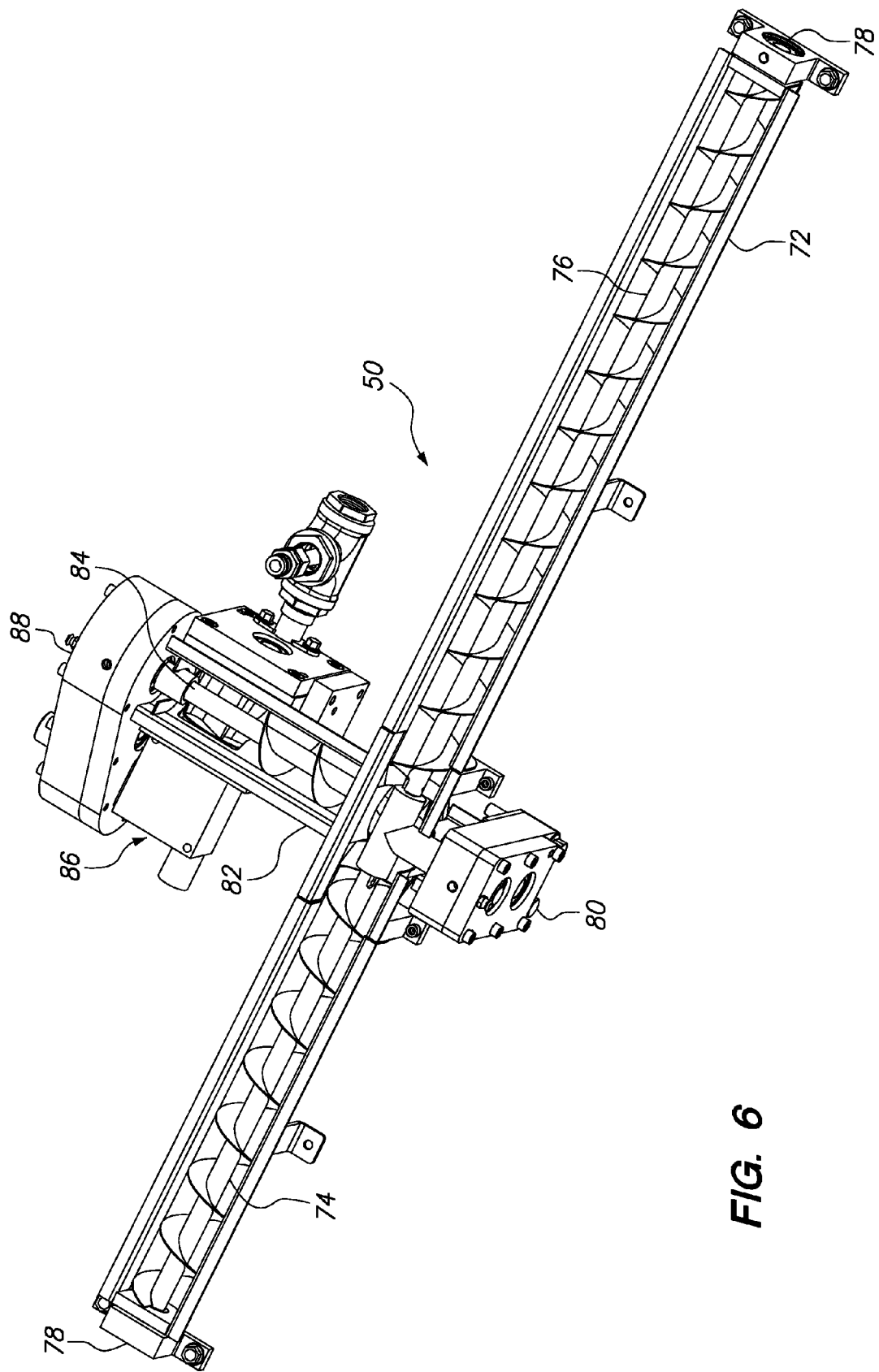
FIG. 6 is a perspective view of a soil receiving assembly according to a preferred embodiment of the present invention.

Turning now to FIG. 6, collection assembly 50 may be described in greater detail. The purpose of collection assembly 50 is to collect soil falling from probe 51 and probe tip 52 as probe assembly 44 passes along the top "rumble path" section of sampler assembly 20. Trough 72 is positioned directly beneath the path of probe assembly 44 for this purpose. The length of trough 72 should preferably be at least as long as the rumble path section through which probe assembly 44 passes, so that whenever soil is shaken loose from within probe 51 it will be caught in trough 72. Within trough 72 are left-hand trough auger 74 and right-hand trough auger 76. Rotation of these augers causes soil that is present in trough 72 to be moved toward the portion of trough 72 where the two augers connect. Bearings 78 support each of these augers at the far ends of trough 72, while they are supported at their interior ends by drive transfer unit 80. Soil that is transferred inward falls through a hole in trough 72 to cross-auger housing 82. Cross-auger 84 rotates to pull soil that has passed into cross-auger housing 82 toward rotor assembly 86. Cross-auger 84 is connected to drive transfer unit 80, thereby providing drive to left hand trough auger 74 and right hand trough auger 76 when it is turning. Drive to cross auger 84 is provided by means of gearbox 88, which acts to provide the proper speed of rotation for the augers of sampler assembly 20. It may be seen then that soil passes from probe 51 to rotor assembly 86 by means of collection assembly 50. As an alternative embodiment, it is also possible to drive longitudinal and cross-augers with hydraulic motors, thus eliminating the need for gearboxes.

Figure 7:
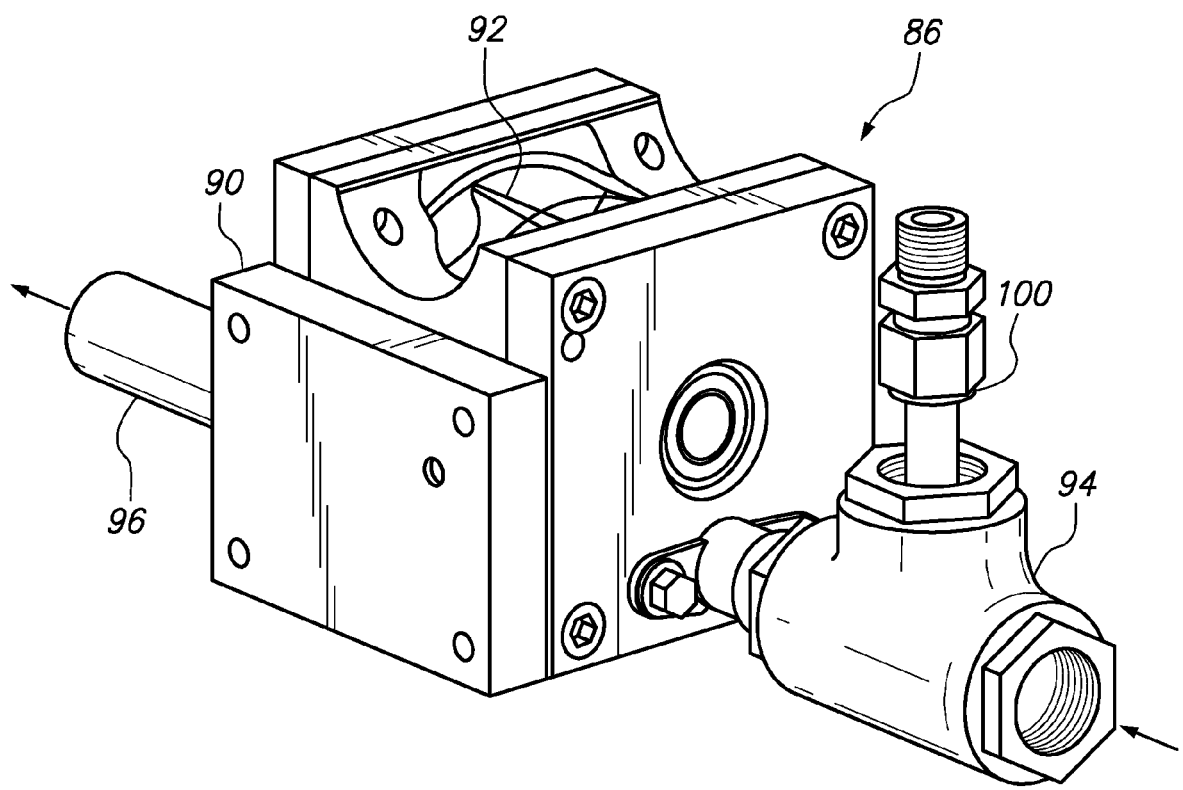
FIG. 7 is a perspective view of a rotor assembly according to a preferred embodiment of the present invention.

Turning now to FIG. 7, rotor assembly 86 may be described in greater detail. Rotor housing 90 contains rotor 92, the purpose of which is to regulate the flow of soil into the pneumatic feed elements of the device, which ultimately deliver soil to bagger assembly 24. Rotor 92 is preferably powered by a hydraulic motor (not shown), as are well known in the prior art. In the preferred embodiment, the upper sidewalls of rotor housing 90 are carved out to match a hole in the bottom of cross-auger housing 82. The blades of rotor 92 extend far enough that they pass into the carved out portion of rotor housing 90, and thus extend into the interior at one end of cross-auger housing 82. As a result, soil that passes through cross-auger housing 82 into rotor assembly 86 does not simply fall into rotor housing 90 from above, but instead is fed directly into the blades of rotor 92 as it moves to the end of cross-auger housing 82 due to the action of cross-auger 84. It is believed that this design provides a more reliable, positive feed of soil samples from cross-auger housing 82 through rotor housing 90. Soil that reaches rotor housing 90 is forced from the top section of rotor housing 90 to the bottom section of rotor housing 90 as a result of the rotation of the blades of rotor 92. Rotor housing inlet 94 provides forced air from blower 48 to rotor housing 90. This air pushes soil that reaches the bottom section of rotor housing 90 into rotor housing outlet 96. The rotor acts as an airlock, thereby feeding soil into an air stream that moves the soil to the operator in the tractor cab.

It has been found that small sticks and like material may occasionally pass through probe 51 and collection assembly 50 to reach rotor housing 90. These obstructions can cause rotor 92 to jam if they catch between a blade of rotor 92 and the edge of the carved out portion of the top wall of rotor housing 90. Therefore, in the preferred embodiment, the blades of rotor 92 are angled slightly with respect to the central axis of rotor 92. It is believed that providing this angle allows the blades of rotor 92 to more easily chop through sticks and like material, helping prevent rotor 92 from jamming during operation. In addition, the controls of the preferred embodiment include a sensor (not shown, such devices being well known in the art) that monitors the rotational velocity of rotor 92. If rotor 92 stops turning due to an obstruction, the controller automatically reverses the direction of the hydraulic motor powering rotor 92 for a short period, allowing the obstruction to pass through before forward operation is resumed. This is particularly useful to allow rocks and such hard materials to pass through the system that might otherwise cause a jam of rotor 92, and which cannot be chopped through by the blades of rotor 92. Control systems capable of providing this functionality, as well as the other functions described herein for control systems of the preferred embodiment, may be implemented in either hardware or as a software application, as well known in the art.

It has also been found that soil may stick to the blades of rotor 92, causing a degradation in the performance of the system. Optionally in a preferred embodiment of the present invention, a high-pressure air inlet 100 may be provided within rotor housing inlet 94. The purpose of high-pressure air inlet 100 is to provide a short burst of high-pressure air, preferably provided by the storage cylinders. The high-pressure burst of air will clear the soil that has clumped around rotor 92, and return the system to proper operation. This functionality may preferably be controlled automatically, high-pressure air inlet 100 releasing a burst of high-pressure air in response to a rise in air pressure within rotor housing inlet 94; high pressure here would indicate a constriction of flow, as would result from soil clumping around rotor 92.

Figure 8A:
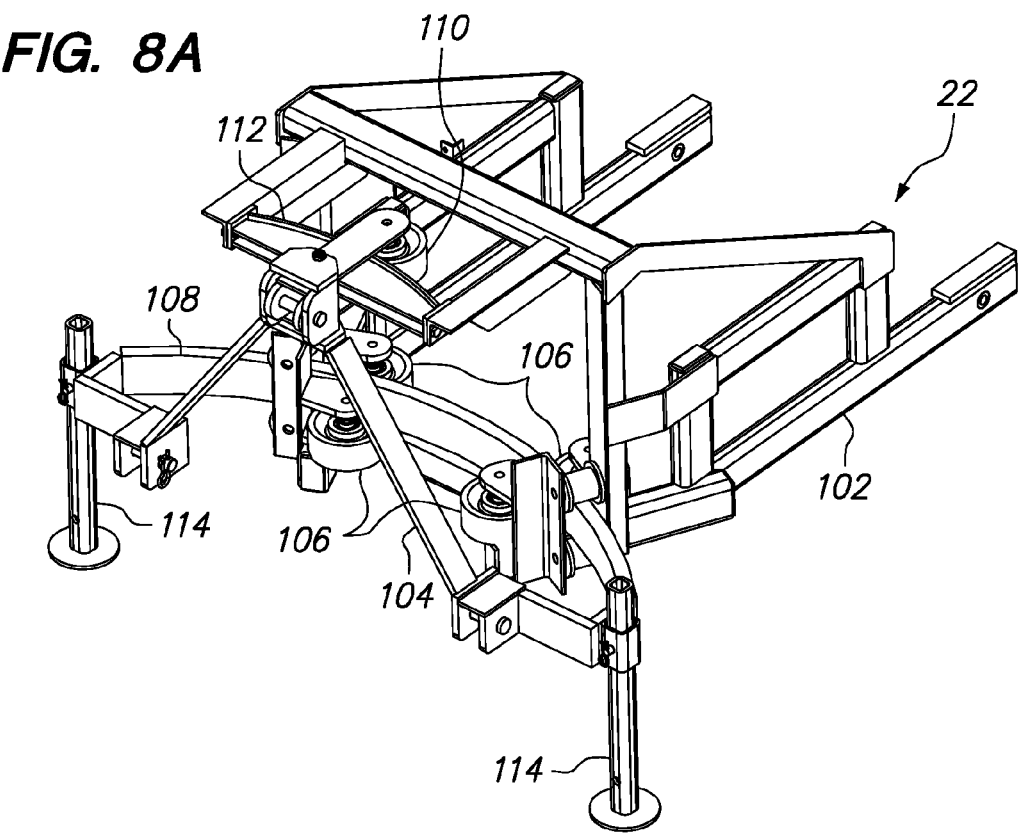
FIG. 8A is a perspective view of a hitch assembly according to a preferred embodiment of the present invention.
Figure 8B:
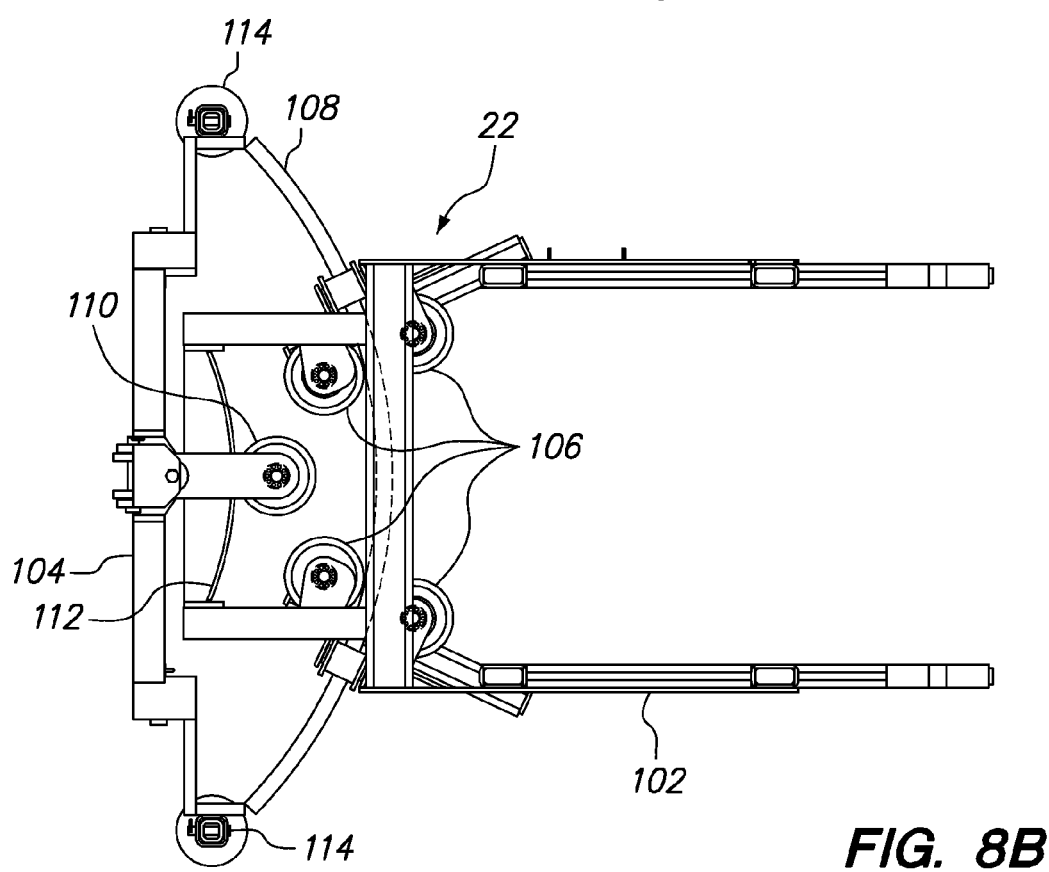
FIG. 8B is a top plan view of a hitch assembly according to a preferred embodiment of the present invention.

Turning now to FIGS. 8A and 8B, hitch assembly 22 according to a preferred embodiment of the present invention may be described. The purpose of hitch assembly 22 is to allow sampler assembly 20 to not only be raised and lowered, as would be the case with any equipment attached behind tractor 26 utilizing a standard three-point hitch mechanism, but also to pivot right and left while remaining in the lowered position. This allows the operator of the device to turn tractor 26 without raising sampler assembly 20 for each turn. Tow frame 102 is the portion of hitch assembly 22 that is connected to sampler assembly 20. Hitch frame 104 connects directly to the three-point hitch assembly of tractor 26. In order to connect tow frame 102 and hitch frame 104, tow frame rollers 106 slide along either side of tow frame roller guide 108, while hitch frame roller 110 slides along the concave side of hitch frame roller guide 112. It may be seen that as tractor 26 executes a turn, the contact between track 29 of sampler assembly 20 and the ground would tend to pull sampler assembly 20 in a straight line. This force will cause tow frame rollers 106 to roll to the corresponding side of tow frame roller guide 108, and hitch frame roller 110 to roll to the corresponding side of hitch frame roller guide 112. In effect, a hinge-like motion is created between the three-point hitch of tractor 26 and sampler assembly 20. Optionally, support legs 114 may be mounted on hitch frame 104 in order to provide support for sampler assembly 20 when not connected to tractor 26, and to facilitate ease of connection between tractor 26 and sampler assembly 20 by holding hitch assembly 22 at the appropriate height to make the necessary connections.

Figure 9:
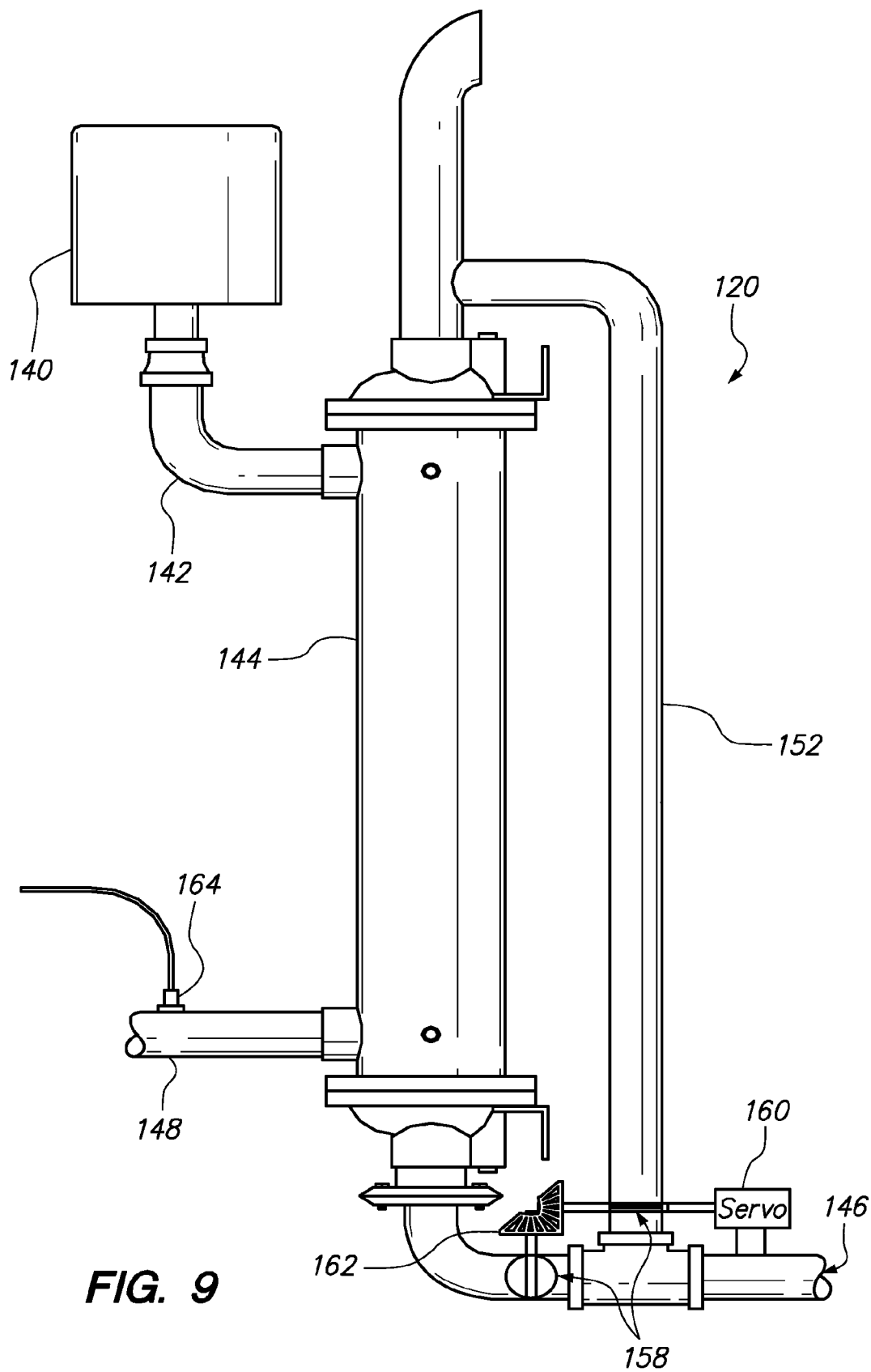
FIG. 9 is a side elevational view of a heat exchanger assembly according to a preferred embodiment of the present invention.

Turning now to FIG. 9, air heater assembly 120 of a preferred embodiment of the present invention may be described. It is believed that providing heated air to rotor housing inlet 94, as shown in FIG. 7, will greatly reduce or eliminate the collection of soil along the walls of the pneumatic pathways employed for soil transfer in the present invention. This is a particular problem when moist soil is being sampled. Wet soil has been found to be far less prone to sticking in pathways if the temperature of the pathway walls is at least around 150° F. Since the exhaust system of tractor 26 provides a source of heat that is well above this temperature, tractor 26 is thus used as a heat source to provide heating for this purpose. As shown in FIG. 9, air intake 140 draws fresh air from the environment at ambient temperature. Air intake pipe 142 delivers this fresh air to heat exchange chamber 144. Tractor exhaust 146 passes through heat exchange chamber 144, such that the hot exhaust gases within exhaust 146 imparts heat to the air within heat exchange chamber 144 as they pass by each other moving in opposite directions. Air outlet 148 delivers the heated air to blower 48, which feeds air to the rest of the pneumatic delivery system as previously described.

In order to regulate the temperature of air traveling to blower 48, a bypass flow system is implemented in the preferred embodiment of the present invention, as illustrated in FIG. 9. Exhaust bypass 152 provides a means for exhaust gases from tractor 26 to bypass heat exchange chamber 144. The degree to which exhaust gases enter bypass 152 is controlled by butterfly valves 158, one of which is located in the path of bypass 152, and the other in the path of tractor exhaust 146 as it enters heat exchange chamber 144. These are controlled by servo 160 and bevel gears 162 such that as one butterfly valve 158 opens, the other closes. Thermostat 164 measures the temperature of air being delivered to blower 48, and a control system uses this temperature measurement to control the opening and closing of butterfly valves 158. As the temperature measured at thermostat 164 goes above the desired temperature for air passing to blower 48, servo 160 will be activated to move butterfly valve 158 in bypass 152 to a more open position, and to move butterfly valve 158 in tractor exhaust 146 to a more closed position. This reduces the temperature of air passing to blower 48, since fewer exhaust gases pass into heat exchange chamber 144 to heat air drawn from air intake 140. If the temperature measured at thermostat 164 drops below a desired temperature, then the opposite result follows in order to raise the temperature of air delivered to blower 48.

Figure 10:
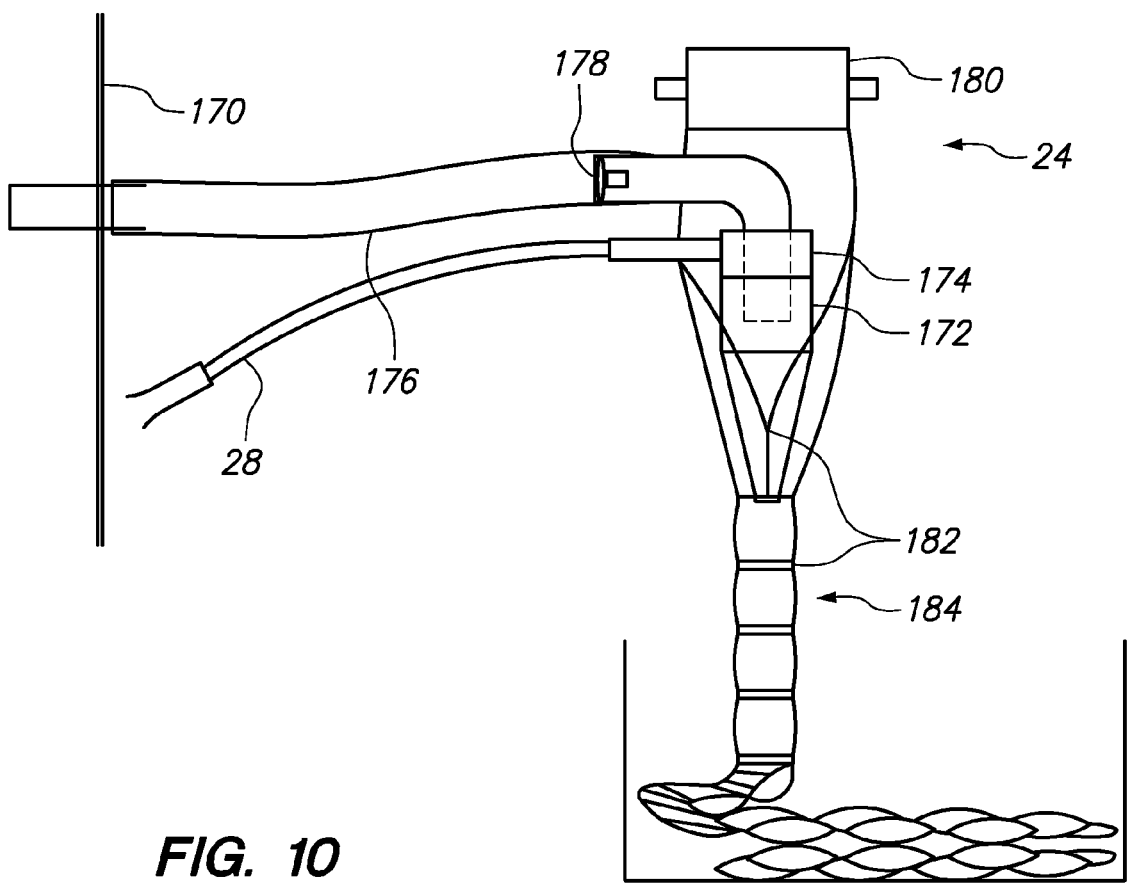
FIG. 10 is a side elevational view, in partial cut-away, of a bagger assembly according to a preferred embodiment of the present invention.

Turning now to FIG. 10, bagger assembly 24 may be described in greater detail. Soil is driven pneumatically by blower 48 from sampler assembly 20 to bagger assembly 24 by means of pneumatic line 28. Pneumatic line 28 delivers the soil to cyclone separator 174. The soil delivered into cyclone separator 174 is swirled along the inner diameter of cyclone separator 174, such that the soil settles downwards toward the apex of the cone portion of cyclone separator 174. Exhaust air outlet 176 provides an outlet for air introduced into cyclone separator 174 through pneumatic line 28. Fan 178 is preferably positioned in exhaust air outlet 176 to provide a small positive pressure to move air out of cyclone separator 174, in order to reduce dust that might otherwise be generated within the cab of tractor 26. Exhaust air outlet 176 preferably passes out through the rear window 170 of tractor 26.

Continuous bagging of soil samples in the preferred embodiment of the present invention is accomplished by means of a bag sealing mechanism and roll of bagging material. Roll 180 provides a continuous feed of tube-shaped bagging material. Heat sealer 182 functions to provide a seal across a portion of the tube-shaped bagging material, forming the bottom of one bag in a continuous link of bags 84. After each sample is collected in the bagging material roll, roll 180 is automatically incremented and heat sealer 182 seals the roll above the top of the sample that has been collected. This seal will also form the bottom of the next bag to be used for collection of the following soil sample, each soil sample thus being stored in separate bags that are linked together in a roll. This arrangement has the advantage that there is no difficulty in keeping track of the order in which samples are collected, since the interconnection of each of the bags formed by the roll will indicate the order in which each sample was taken. Optionally, the operator of tractor 26 may label each of the bags or rolls of bags as sampling takes place.

In a preferred method according to the present invention, a grower may perform sampling over a field of interest utilizing mapping software and global positioning system (GPS) satellite information to highly automate the sampling process. For example, consider a square field of interest that of a size of 64 hectares. This field may be mapped using a GPS receiver and mapping software, with a tractor that simple travels the perimeter of the field. Such software is commercially available from companies such as Raven Industries of Sioux Falls, S.D., and Trimble Navigation Limited of Sunnyvale, Calif. The field may then be divided into, for example, sixty-four sections from which unique samples will be analyzed, using a grid that is overlaid by software onto the resulting field map. Each of the sampling sections will thus be of a size of 1 hectare.

In order to collect samples, the operator attaches sampler assembly 20 to tractor 26 by means of hitch assembly 22, including the connection of pneumatic line 28 to bagger assembly 24 mounted in the cab of tractor 26. Sampler assembly 20 may be raised using hitch assembly 22, and tractor 26 proceeds to the edge of the field of interest. Tractor 26 then moves back and forth across the field. Tractor 26 may be manually guided by the operator, or the operator may take advantage of autosteer technology using GPS information, which is incorporated into many farm tractors now produced, or may be part of a guidance system installed for use with the system. Ground cores are periodically, and automatically, taken as the field is traversed. The GPS receiver of tractor 26 constantly monitors the location of sampler assembly 20, and the onboard controller may be programmed to send a signal to bagger assembly 26 as each grid line is crossed. In this way, multiple cores are automatically taken from each sampling section, while the cores are deposited in separate bags formed from bag roll material 180, without any further action by the operator. The operator need only stop when bag roll material 180 needs to be replenished, and a new roll of bagged soil samples will be begun. When sampling is complete, the operator may raise sampler assembly 20 with respect to tractor 26, and drive tractor 26 back to a storage area.

It should be noted that while the size of a field of interest and a sample area has been described with respect to the preferred embodiment, the invention may be employed in a field of any size, and sampling areas may be either increased or decreased in size based on the accuracy desired and the time in which the operator has available to perform the sampling operation. As described above, once the sections of the field of interest increase to a certain size, it may be preferable to only collect cores on every second revolution of probe assembly 44, every third revolution of probe assembly 44, or some other multiple of the number of revolutions. The inventors have found that roughly 50 cores are required to form a sample that has a mass of about 1 kg. Since the preferred sample size is around 0.25 kg, approximately 20 cores should be taken for each sample when using the preferred embodiment of the invention. The size of the bags formed from bag roll material 180 should preferably be sized so that they can easily receive at least this number of cores.

The present invention has been described with reference to certain preferred and alternative embodiments that are intended to be exemplary only and not limiting to the full scope of the present invention as set forth in the appended claims.

What is claimed is:

1. A soil sampling apparatus, comprising:
   (a) a sampling assembly frame;
   (b) a rotational drive member mounted to said frame
   (c) a probe assembly attached to said rotational drive member; and
   (d) a probe assembly track, wherein said probe assembly is operable to follow said probe assembly track to rotate around said frame with said rotational drive member, and wherein said probe assembly comprises a probe operable to extend into a section of soil and retract a sample from the section of soil.

2. The soil sampling apparatus of claim 1, further comprising a vehicle and a hitch assembly removably attaching said soil sampling frame to said vehicle.

3. The soil sampling apparatus of claim 2, wherein said hitch assembly comprises a tow frame connected to said soil assembly frame, a hitch frame connected to said vehicle, at least one roller in communication with at least one of said hitch frame and said tow frame, and at least one roller guide in communication with at least the other one of said hitch frame and said tow frame, wherein said roller is positioned to roll against said roller frame whereby said soil assembly frame may pivot with respect to said vehicle.

4. The soil sampling apparatus of claim 1, wherein said probe assembly comprises a probe roller and a follower roller, and said track comprises a probe track and a follower track, wherein said probe roller is positioned to roll within said probe track and said follower roller is positioned to roll within said follower track as said probe assembly rotates around said frame with said rotational drive member.

5. The soil sampling apparatus of claim 4, wherein said probe assembly further comprises a scissor arm connected to said probe, wherein said scissor arm is operable to straighten as said probe extends from said rotational drive member, and said scissor arm is operable to retract as said probe retracts into said rotational drive member.

6. The apparatus of claim 4, wherein said probe track comprises an upward probe track that extends around a rear section of the sampling assembly, and wherein said upward probe track comprises a first curved section, whereby passage of said probe roller through said rearward probe track first curved section causes said probe to turn upward.

7. The soil sampling apparatus of claim 4, wherein said probe track comprises a forward probe track, which extends from a front position with respect to said sampling assembly to a middle position with respect to said sampling assembly, and said forward probe track is progressively closer to said follower track between the front position and the middle position, whereby said probe is extended as said probe roller follows said forward probe track and said follower roller follows said follower track between the front position and the middle position.

8. The soil sampling apparatus of claim 7, further comprising at least one load cell mounted in communication with a probe track, wherein said load cell is operable to send a signal causing said probe not to extend as said probe follower passes along said forward probe track if a pressure sensed at said probe and communicated by said signal exceeds a threshold value.

9. The soil sampling apparatus of claim 8, further comprising a control system operable to store a soil compaction value corresponding to said signal in a digital data storage medium.

10. The soil sampling apparatus of claim 4, wherein said probe track comprises a rearward probe track, which extends from a middle position with respect to said sampling assembly to a rear position with respect to said sampling assembly, and said rearward probe track is progressively further from said follower track between the middle position and the rearward position, whereby said probe is retracted as said probe roller follows said rearward probe track and said follower roller follows said follower track between the middle position and the back position.

11. The apparatus of claim 10, wherein said rearward probe track is curved.

12. The apparatus of claim 11, wherein the curvature of said rearward probe track is operable to provide an approximately constant acceleration with respect to said probe as it retracts between the middle position and the back position.

13. The apparatus of claim 4, wherein said probe track comprises a top probe track, wherein said top probe track comprises at least one irregularity, whereby said probe is moved rapidly in an approximately vertical direction as said probe roller passes through said top probe track.

14. The apparatus of claim 13, wherein said top probe track comprises a plurality of irregularities.

15. The soil sampling apparatus of claim 13, further comprising a collection assembly positioned beneath said top probe track, wherein said probe is operable to drop a soil sample from said probe into said collection assembly as said probe roller passes through said top probe track.

16. The soil sampling apparatus of claim 15, wherein said probe comprises a tapered inner diameter.

17. The soil sampling apparatus of claim 15, further comprising a bagger assembly and a pneumatic line connecting said collection assembly to said bagger assembly.

18. The soil sampling apparatus of claim 17, wherein said bagger assembly comprises a cyclone operable to separate soil from air.

19. The soil sampling apparatus of claim 18, wherein said bagger assembly further comprises a bag roll feeder operable to feed a roll of bag material to said cyclone and a bag sealer whereby soil samples falling from said cyclone are individually bagged.

20. The soil sampling apparatus of claim 15, wherein said collection assembly comprises:

(a) at least one trough;
(b) a rotor housing positioned beneath said trough at an opening in said trough, whereby said rotor housing may receive the soil sample from said trough; and
(c) a rotor rotationally mounted within said rotor housing.

21. The soil sampling apparatus of claim 20, wherein said rotor comprises an axis and a plurality of blades, wherein each of said blades is positioned at an angle with respect to a line parallel to said rotor axis.

22. The soil sampling apparatus of claim 20, wherein said rotor blades rotate to extend at least partially within said trough of said collection assembly.

23. The soil sampling apparatus of claim 20, further comprising a hydraulic motor in fluid communication with said rotor and operable to drive said motor, and a rotation sensor, wherein said hydraulic motor is operable to reverse the direction of drive to said motor in response to a signal from said rotation sensor indicating that a rotational speed of said rotor has fallen below a threshold rotational speed.

24. The soil sampling apparatus of claim 20, further comprising an air inlet and air outlet connected to said rotor housing.

25. The soil sampling apparatus of claim 24, further comprising a high-pressure air inlet within said air inlet operable to release a burst of high-pressure air through said rotor housing.

26. The soil sampling apparatus of claim 24, further comprising a heater operable to heat air delivered to said air inlet.

27. The soil sampling apparatus of claim 26, wherein said heater comprises an exhaust and a heat exchanger positioned to draw heat from said exhaust into air passing through said heat exchanger toward said air inlet.

* * * * *